United States Patent
Rosenstein et al.

(10) Patent No.: US 11,828,742 B2
(45) Date of Patent: Nov. 28, 2023

(54) MULTI-PARAMETRIC MACHINE OLFACTION

(71) Applicant: Brown University, Providence, RI (US)

(72) Inventors: Jacob K. Rosenstein, Providence, RI (US); Christopher Rose, Providence, RI (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

(21) Appl. No.: 18/170,849

(22) Filed: Feb. 17, 2023

(65) Prior Publication Data

US 2023/0251238 A1 Aug. 10, 2023

Related U.S. Application Data

(63) Continuation of application No. 16/589,668, filed on Oct. 1, 2019, now Pat. No. 11,592,427.

(60) Provisional application No. 62/739,728, filed on Oct. 1, 2018.

(51) Int. Cl.
*G01N 33/00* (2006.01)
*B81B 3/00* (2006.01)

(52) U.S. Cl.
CPC ....... *G01N 33/0075* (2013.01); *B81B 3/0018* (2013.01); *B81B 2201/0264* (2013.01); *B81B 2201/0278* (2013.01)

(58) Field of Classification Search
CPC .............. G01N 33/0075; B81B 3/0018; B81B 2201/0264; B81B 2201/0278
See application file for complete search history.

(56) References Cited

U.S. PATENT DOCUMENTS

| | | | |
|---|---|---|---|
| 5,832,411 A | 11/1998 | Schatzmann et al. | |
| 6,636,811 B1 | 10/2003 | Walte et al. | |
| 6,649,416 B1 | 11/2003 | Kauer et al. | |
| 6,816,301 B1 | 11/2004 | Schiller | |
| 7,477,994 B2 | 1/2009 | Sunshine et al. | |
| 8,695,401 B2 | 4/2014 | Wang et al. | |
| 8,707,760 B2 | 4/2014 | Chou et al. | |
| 8,978,444 B2 | 3/2015 | Chou et al. | |
| 8,999,245 B2 | 4/2015 | Wang et al. | |
| 9,725,751 B2 | 8/2017 | Moularat et al. | |
| 2002/0045272 A1 | 4/2002 | McDevitt et al. | |
| 2003/0051023 A1 | 3/2003 | Reichel et al. | |
| 2004/0101851 A1 | 5/2004 | White et al. | |
| 2004/0204915 A1* | 10/2004 | Steinthal | B82Y 30/00 702/30 |

(Continued)

FOREIGN PATENT DOCUMENTS

WO 2014111611 A1 7/2014

OTHER PUBLICATIONS

Shakya, et al., "Time Series Feature Extraction for Machine Olfaction", 10.1109/SENSORS43011.2019.8956519, 2019, pp. 1-4.

(Continued)

*Primary Examiner* — David J Bolduc
(74) *Attorney, Agent, or Firm* — Adler Pollock & Sheehan P.C.

(57) ABSTRACT

A system includes an array of chemical, pressure, and temperature sensors, and a temporal airflow modulator configured to provide sniffed vapors in a temporally-modulated sequence through a plurality of different air paths across multiple sensor locations.

8 Claims, 5 Drawing Sheets

(56) References Cited

U.S. PATENT DOCUMENTS

| | | |
|---|---|---|
| 2010/0225337 A1 | 9/2010 | Zamborini et al. |
| 2010/0229658 A1 | 9/2010 | Glezer et al. |
| 2013/0304385 A1 | 11/2013 | Gillette |
| 2015/0022357 A1 | 1/2015 | Gettings et al. |
| 2015/0094219 A1 | 4/2015 | Trowell et al. |
| 2015/0185161 A1 | 7/2015 | Gettings et al. |
| 2015/0302728 A1 | 10/2015 | Gettings et al. |
| 2016/0302729 A1 | 10/2016 | Starr et al. |
| 2018/0120278 A1 | 5/2018 | Hoorfar et al. |
| 2018/0364207 A1 | 12/2018 | Roberts et al. |
| 2019/0072529 A1 | 3/2019 | Andrawes et al. |
| 2020/0100115 A1 | 3/2020 | Skaaksrud |
| 2020/0264088 A1 | 8/2020 | Bentley |

OTHER PUBLICATIONS

Webster, et al., "TruffleBot: Low-Cost Multi-Parametric Machine Olfaction", 1109/BIOCAS.2018.8584767, 2018, pp. 1-4.

\* cited by examiner

TABLE I
SENSOR ARRAYS FOR ODOR CLASSIFICATION

| | Sensors | Measured Parameters | Array Size | Time Series | Analytes | Classification |
|---|---|---|---|---|---|---|
| This work | Metal oxide & Mechanical | chemical, pressure, temperature | 8 (x3) | Yes | 8 | PCA |
| Wang, 2017 [19] | Metal oxide | chemical | 12 | No | 5 | PNN |
| Harun, 2009 [18] | Chemoresistive | chemical | 900 | No | 4 | PNN |
| Wojnowski, 2017 [9] | Electrochemical | chemical | 7 | No | 8 | SVM |
| Shulaker, 2017 [10] | Carbon nanotube FET | chemical | 2048 | No | 7 | PCA |

FIG. 6

MULTI-PARAMETRIC MACHINE OLFACTION

CROSS REFERENCE TO RELATED APPLICATIONS

This application is a continuation of U.S. patent application Ser. No. 16/589,668, filed Oct. 1, 2019, which claims benefit from U.S. Provisional Patent Application Ser. No. 62/739,728, filed Oct. 1, 2018, each of which is incorporated by reference in its entirety.

STATEMENT REGARDING GOVERNMENT INTEREST

This invention was made with government support under agreement HR00111720048 awarded by the DARPA Defense Sciences Office. The government has certain rights in the invention.

BACKGROUND OF THE INVENTION

The present invention relates generally to machine olfaction, and more particularly to multi-parametric machine olfaction.

In general, machine olfaction is the automated simulation of the sense of smell. A sense of smell is one of the most fundamental ways that animals interact with the world Most animals actively sample ambient odors by sniffing, which introduces chemical samples to the olfactory receptors of the nose, and these receptors in turn generate signals that are decoded by the brain. Many groups have worked towards bio-inspired machine olfaction, particularly through the statistical interpretation of a diversity of chemical measurements. However, an important insight into the biological process is that the brain takes advantage of many types of non-chemical information when analyzing odors, including temporal, spatial, mechanical, hedonic, and contextual correlations. In contrast, engineered chemical sensors often ignore this ancillary information. Environmental conditions, when measured, are often considered only in the context of calibrating chemical measurements.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention features a system including an array of chemical, pressure, and temperature sensors, and a temporal airflow modulator configured to provide sniffed vapors in a temporally-modulated sequence through a plurality of different air paths across multiple sensor locations.

In another aspect, the invention features a system including an array of eight sensor pairs arranged in four rows of two, each pair of sensors including one Volatile Organic Compound (VOC) sensor and one digital barometer, a digital-to-analog converter (DAC) whose voltage controls the temperature of each of the sensor pairs, a Digital-to-Analog Converter (DAC), and a Raspberry Pi configured to provide power to the array eight sensor pairs, and to wirelessly transmits data from the array of sensor pairs to a host computer configured to analyze the data.

In still another aspect, the invention features a system including a pump regulated to a constant airflow by a flow controller, a three-way solenoid valve configured to selectively pass the airflow and an analyte vapor, and a manifold configured to split the airflow containing analyte vapor between four small plastic columns containing different obstructions before reaching a sensing unit.

In yet another aspect, the invention features a method including providing an analyte, passing vapor of the analyte through a three-way solenoid valve configured to selectively pass an airflow and the analyte vapor, and passing the analyte vapor through a manifold configured to split the airflow containing analyte vapor between four small plastic columns containing different obstructions before reaching a sensing unit for analysis.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

FIG. 6 is a table.

DETAILED DESCRIPTION

Figure 1:
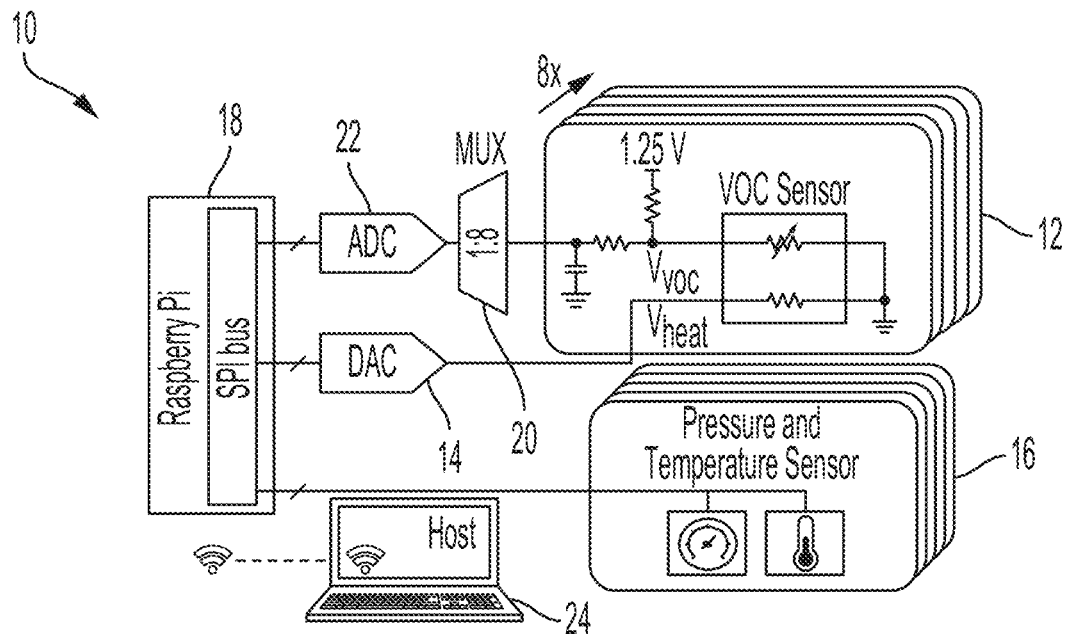
FIG. 1 is a block diagram of an exemplary system.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

Most implementations of electronic noses ("e-noses") include an array of chemical sensors whose outputs are analyzed in parallel at one discrete point in time. These designs are widely employed across military, industrial, medical, and environmental sciences, with applications ranging from explosives and disease detection to environmental and industrial monitoring. Recent advances in compact, portable, and low-cost sensor designs have been complemented by aggressive microelectronic integration.

The present invention is an electronic platform (sometimes referred to herein as "TruffleBot") which classifies odors using multi-parametric environmental information in order to improve upon traditional e-noses. The TruffleBot simultaneously samples pressure, temperature, and chemical time series, while "sniffing" in a temporally modulated sequence which introduces spatiotemporal time signatures, such as transport delays and diffusive dynamics. These multidimensional signals depend on chemical and physical properties which can be unique to a particular chemical. Additionally, the odor plumes traverse a set of four unique physical pathways which have the aggregate effect of expanding the feature space and separability of odors. The system, which mirrors some of the dynamic contextual features of animal olfaction, improves the performance and accuracy of chemical sensing in a simple and low-cost hardware platform.

In FIG. 1, a block diagram of an exemplary system 10 is illustrated. Eight analog metal-oxide gas sensors 12 are digitized while a DAC 14 controls their heater voltage while eight digital barometers 16 measure pressure and temperature. The array of eight sensor pairs 12, 16 are arranged in four rows of two, with each position containing one Volatile Organic Compound (VOC) sensor and one digital barometer. The array of eight sensor pairs 12, 16 are linked to a Raspberry Pi 18 (85 mm×56 mm).

The VOC sensors 12 (e.g., AMS CCS801) are microhotplate metal-oxide (MOX) sensors with integrated resistive heaters. In a MOX gas sensor, a metal oxide film is heated to several hundred degrees Celsius, to a temperature where its electrical conductivity becomes sensitive to chemical interactions with nearby gases. These interactions are complex and non-specific, and MOX sensors will respond to the presence of many different volatile molecules. The heaters of the eight MOX sensors are driven from the common buffered DAC 14, whose voltage controls the temperature of the sensors, and in turn, affects their chemical sensitivity. The MOX resistivity is converted to a voltage and routed through a multiplexer 20 into a high precision ADC 22 (e.g., TI ADS1256). Components 12, 14, 16, 18, 20 and 22 are referred to herein collectively as a "TruffleBot."

In one embodiment, the digital barometers (e.g., ST LPS22HB) are small MEMS sensors with piezoresistive elements on a thin suspended membrane. These chips measure both temperature and absolute pressure at up to 75 samples per second through a serial peripheral interface (SPI) bus.

The TruffleBot is powered entirely through the 5V and 3.3V rails of a Raspberry Pi 18, and consumes approximately 77 mW. The TruffleBot also hosts several other supporting circuits, including a precision reference generator for the MOX sensors, and transistors to switch external 5V peripherals which may include solenoids and small air pumps. Other peripherals can also be connected through a Universal Serial Bus (USB) (not shown). Components for one TruffleBot cost approximately $150 US.

The TruffleBot connects to a host computer 24 over Ethernet or WiFi, and multiple TruffleBots can co-exist on the same network. A host program initiates an experiment by broadcasting a command for all TruffleBots to begin data collection. Each TruffleBot saves its sensor traces locally, and when the trial concludes, the host automatically retrieves each client's dataset and compiles them all into a single HDFS file for analysis in MATLAB™ from The Mathworks.

Figure 2:
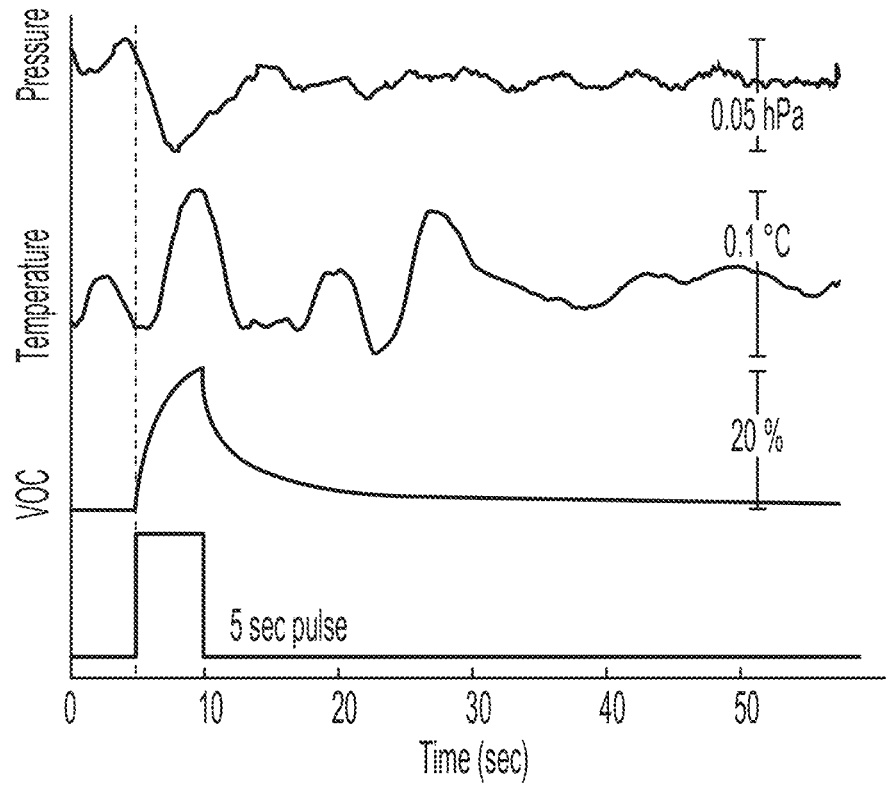
FIG. 2 is an exemplary graph.

FIG. 2 is an exemplary graph that plots the temperature, pressure and chemical response to a five second exposure to odors from beer (≈6% ethanol). The output of the VOC sensor is expressed as a percentage of its full scale range, and the pressure and temperature signals deviate only slightly from ambient. When beer odors are introduced, the pressure decreases and the temperature increases; both the polarity and magnitude of these changes depend on the physical properties of the analyte vapor including its vapor pressure, density, and molecular weight. These differences contribute to TruffleBot's overall chemical selectivity.

Figure 3:
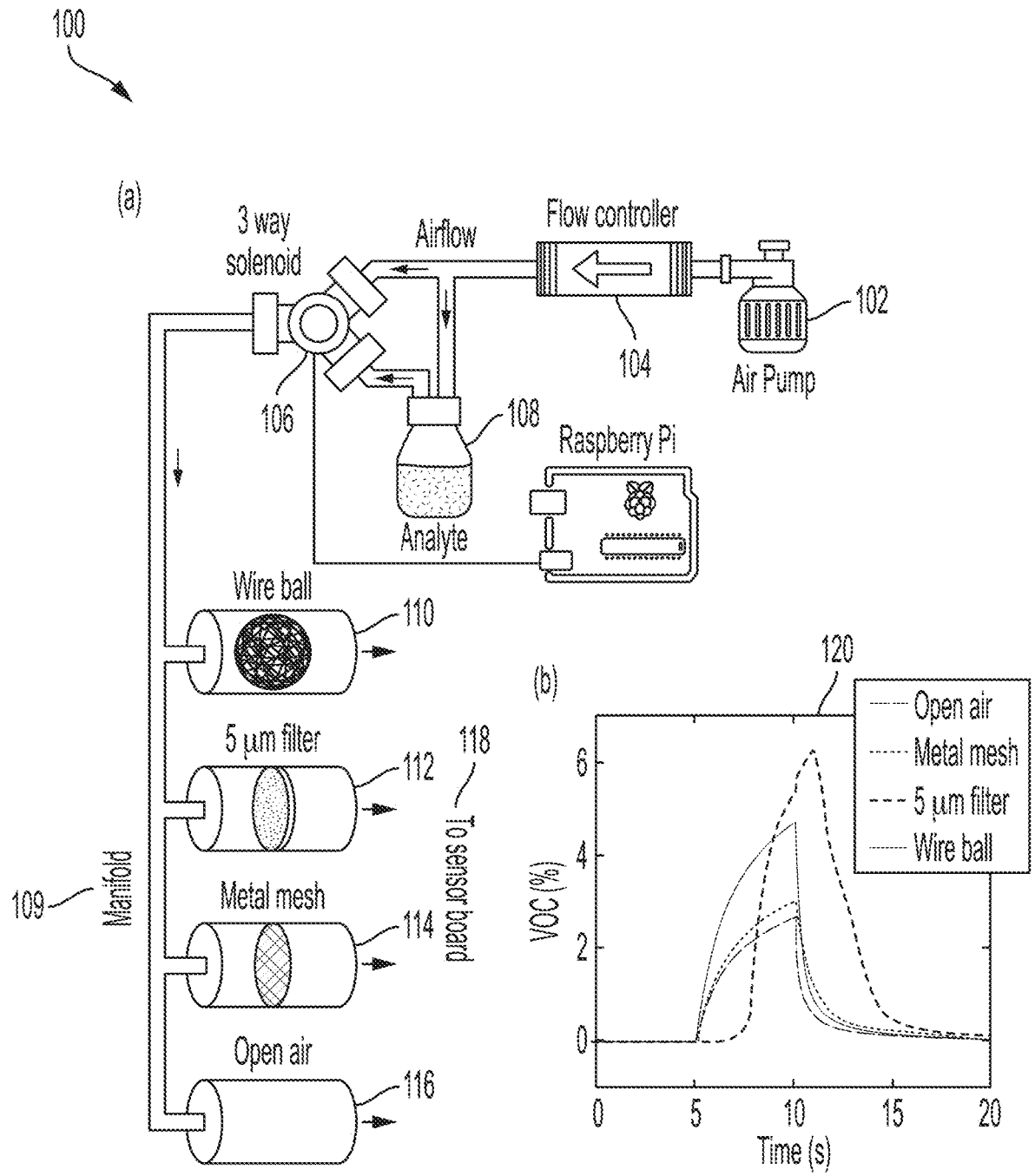
FIG. 3 is an exemplary test bench.

In FIG. 3, an exemplary test bench 100 is illustrated in (a). The output of a pump 102 is regulated to a constant flow by a flow controller 104, and a three-way solenoid valve 106 (e.g., Takasago CTV-3) selectively bypasses the analyte vapor 108. The solenoid 106 is controlled with a short pseudorandom (PN) binary sequence. The analytes used in these experiments were ambient air (control), apple cider vinegar, lime juice, beer (6.2% ABV), wine (chardonnay, 13% ABV), vodka (40% ABV), ethanol (100% ABV), isopropanol, and acetone. A manifold 109 splits the fluid flow between four small plastic columns 110, 112, 114, 116 containing different obstructions before reaching the sensor array 118. This arrangement allows one to adjust multiple parameters including the overall airflow, the solenoid's temporal sequence, the analyte, and the geometries and contents of the columns.

In (b), an exemplary graph 120 shows differences in the positions and obstructions of four air paths produce different signals in each column, in response to ethanol.

Figure 4:
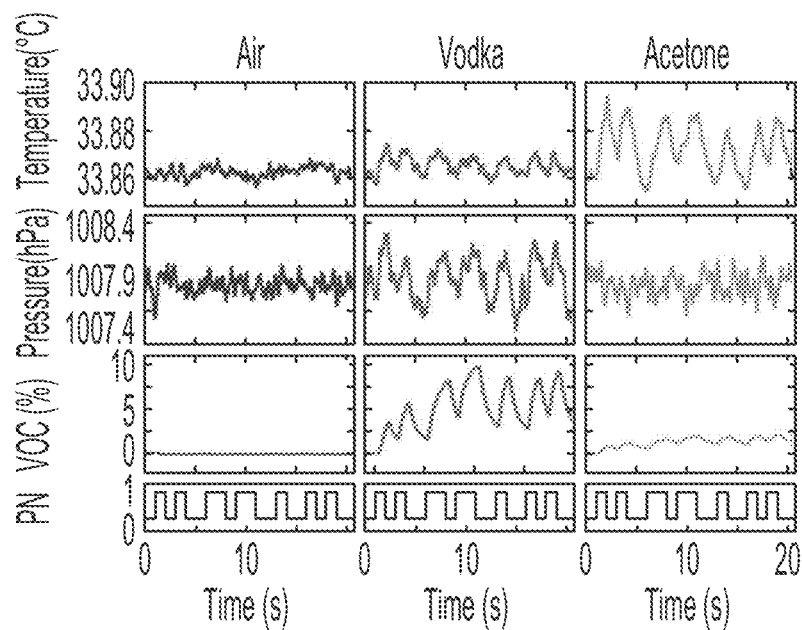
FIG. 4 is an exemplary comparison.

FIG. 4 shows an exemplary comparison of the responses to air, vodka and acetone, at a single array position. The baseline signal levels are affected by noise and uncontrolled parameters including ambient temperature, humidity, and atmospheric pressure. The solenoid PN sequence is the same for all trials, and the signal is represented by temporally correlated changes in the sensor outputs. Assuming a lossless system with fixed volumetric flow, the total absolute pressure in each column head can be represented as $$P_{abs} = P_{atm} + P_{ext} + P_{analyte} \quad (1)$$

where $P_{ext}$ is the resulting pressure from the constant regulated airflow and $P_{atm}$ and $P_{analyte}$ are the partial pressures exerted by atmospheric air and the analyte vapor. (When the solenoid bypasses the analyte, $P_{analyte}=0$.) According to the Darcy-Weisbach equation, Newtonian fluid flowing through a cylindrical tube experiences a pressure drop given by $$\Delta p = \rho f L v^2 / 2D \quad (2)$$

where $\rho$ is the fluid density, v is the fluid velocity and f, L, D are the friction coefficient, length, and diameter of the tube. Since the flow is constant and tube properties do not change, $\Delta p$ only depends on $\rho$. Thus an analyte with vapor density greater than air would incur more pressure loss in the tube, resulting in a decrease in measured air pressure. For example, $P_{abs}$ decreases during the release of beer ($\rho=1.05$ g/cm$^3$) but increases for vodka ($\rho=0.95$ g/cm$^3$).

These pressure changes, in combination with the analyte's physical properties (e.g. heat capacity), produce analyte-specific temperature fluctuations. Using this information, TruffleBot can distinguish between analytes which have similar MOX sensor responsivity, provided the pressure and temperature changes observed are a systematic result of the analyte's physical properties. For example, in FIG. 4, vodka and acetone could have been easily discriminated by temperature and pressure alone.

Figure 5A:
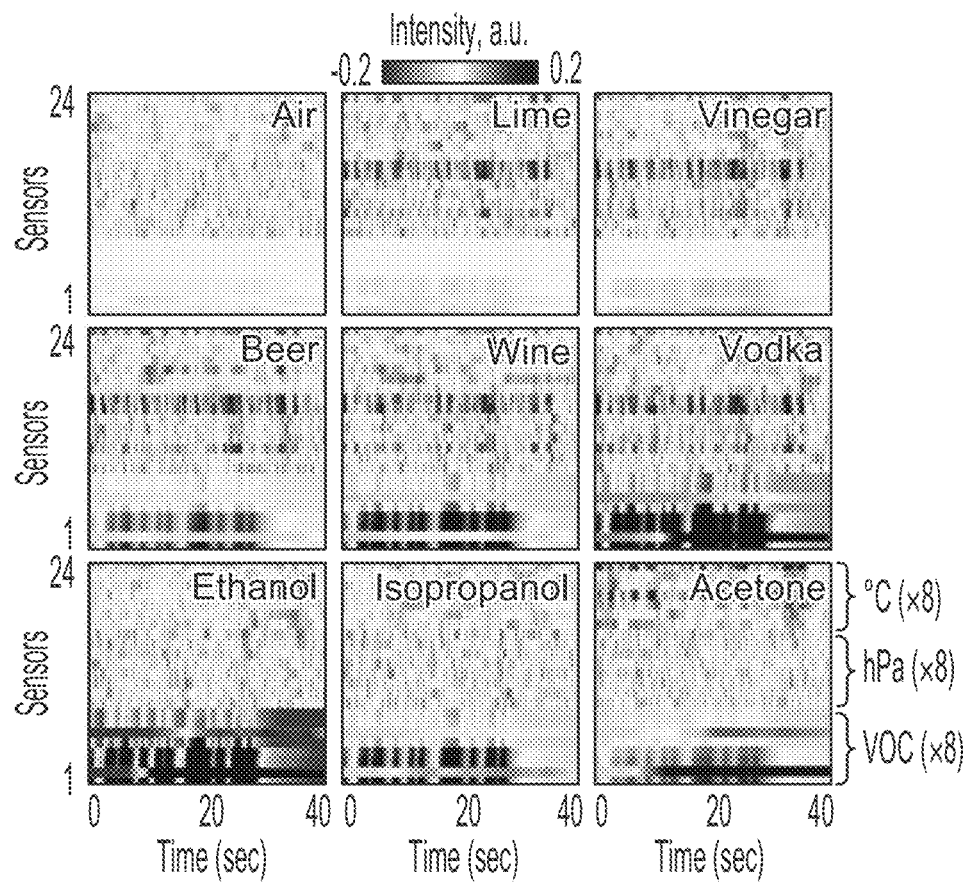
FIGS. 5(a), 5(b) and 5(c) illustrate representative data for odors.

The arrayed sensors and diverse airflow paths support the extraction of temporal and spatial features. Using the setup in FIG. 3, the same "sniffing" sequence of 40 pseudorandom bits was applied at 1 bit/second for 8 different analytes. Representative data for each odor is shown in FIG. 5(a). The first eight rows represent VOC sensor traces, followed by eight rows of pressure readings and eight rows of temperature readings. The mean value has been subtracted from each trace. The control trials with ambient air show only small deviations, while VOC magnitudes appear to correlate with alcohol content, as one might anticipate. Some odors do not have significant VOC sensor response (lime, vinegar), but do show appreciable pressure and temperature responses.

Figure 5B:
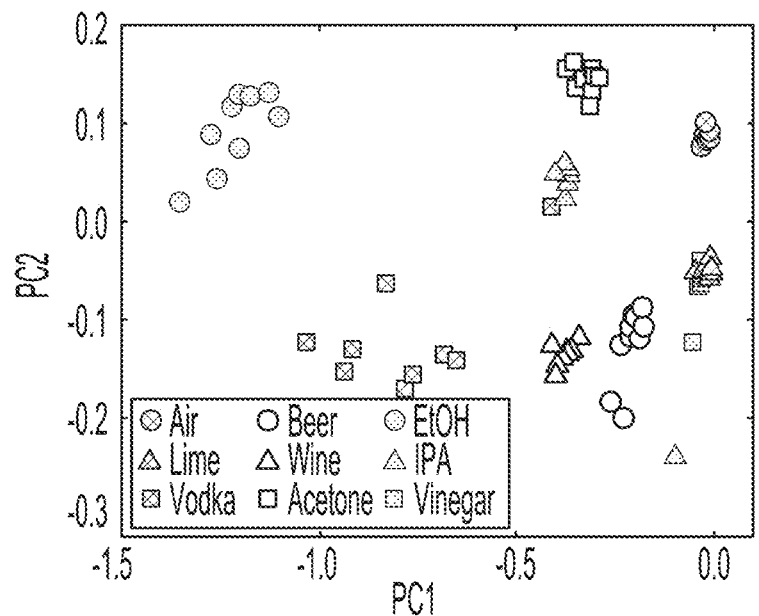

The experiment was repeated ten times for each analyte, and feature vectors containing the mean, derivative, and standard deviation were assembled from 0.5 second windows of each of the 24 time series. We performed principal-component analysis (PCA) on the combined sensor data of the nine odor classes (FIG. 5(b)). Even with a comparison of only the first two principal components, tightly grouped clusters emerged. We then performed 2-fold cross-validation of the results using a simple k-means algorithm over 1000 iterations. The classification approach is comparable to other e-nose demonstrations, and is one of many possible classification strategies (See Table I in FIG. 6).

Figure 5C:
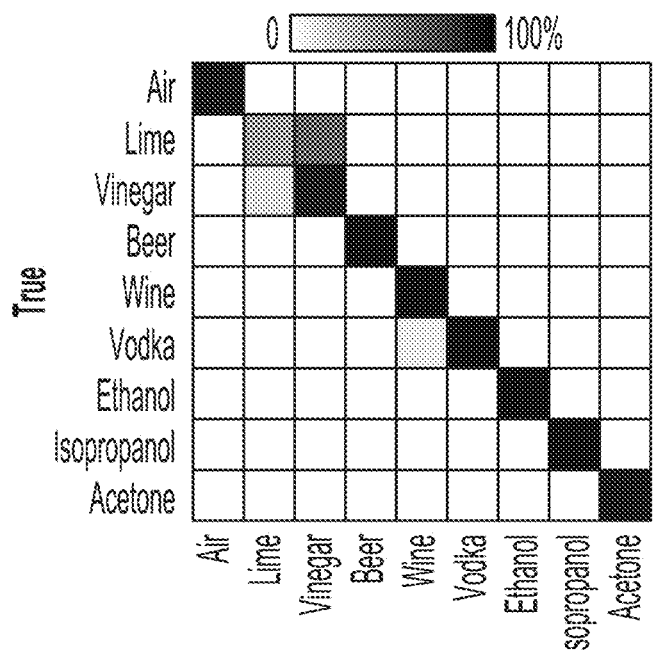

A cross validation accuracy of 90.9% was achieved using only the transient time series from the MOX sensors, compared to 79.8% if the data is condensed to only 1 average value per MOX sensor. Adding temperature and pressure data, error rates reduced by a factor of 2 and accuracy improved to 95.8%. The confusion matrix in FIG. 5(c) shows that most of the errors occurred between lime and vinegar. This can also be seen in their overlapping PCA clusters (FIG. 5(b)), and it is intuitive since citric acid and acetic acid contain chemically similar functional groups. Repeating the classification for the 8 datasets excluding lime gives a cross validation accuracy of 98.5%.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A system comprising:
    an array of chemical, pressure, and temperature sensors, the array of chemical, pressure, and temperature sensors comprising an array of sensor pairs; and
    a temporal airflow modulator configured to provide sniffed vapors in a temporally-modulated sequence through a plurality of different air paths across multiple sensor locations.

2. The system of claim 1 wherein each pair of sensors comprising one Volatile Organic Compound (VOC) sensor and one digital barometer.

3. The system of claim 2 wherein each VOC sensor comprises a micro-hotplate metal-oxide (MOX) sensor with integrated resistive heaters configured to respond to a presence of volatile molecules.

4. The system of claim 3 wherein each digital barometer comprises a small MEMS sensor with piezoresistive elements on a thin suspended membrane.

5. A system comprising:
    an array of sensor pairs;
    a Digital-to-Analog Converter (DAC) whose voltage controls the temperature of each of the sensor pairs; and
    a series of single-board computers configured to provide power to the array of eight sensor pairs, and to wirelessly transmits data from the array of sensor pairs to a host computer configured to analyze the data.

6. The system of claim 5 wherein each pair of sensors comprising one Volatile Organic Compound (VOC) sensor and one digital barometer.

7. The system of claim 6 wherein each VOC sensor comprises a micro-hotplate metal-oxide (MOX) sensor with integrated resistive heaters configured to respond to a presence of volatile molecules.

8. The system of claim 7 wherein each digital barometer comprises a small MEMS sensor with piezoresistive elements on a thin suspended membrane.

* * * * *